US006589178B2

(12) United States Patent
Sakai (10) Patent No.: US 6,589,178 B2
(45) Date of Patent: Jul. 8, 2003

(54) METHOD OF ESTIMATING BONE MINERAL DENSITY AND APPARATUS FOR ESTIMATING BONE MINERAL DENSITY

(75) Inventor: Nobuya Sakai, Tokyo (JP)

(73) Assignee: Tanita Corporation, Tokyo (JP)

( * ) Notice: Subject to any disclaimer, the term of this patent is extended or adjusted under 35 U.S.C. 154(b) by 0 days.

(21) Appl. No.: 10/076,521

(22) Filed: Feb. 19, 2002

(65) Prior Publication Data

US 2002/0156378 A1 Oct. 24, 2002

(30) Foreign Application Priority Data

Feb. 19, 2001 (JP) ........................................ 2001-041318

(51) Int. Cl.$^7$ ................................................ A61B 8/00
(52) U.S. Cl. ........................ 600/449; 600/442; 600/443; 73/592; 73/597
(58) Field of Search ................................ 600/437, 442, 600/449, 407, 443; 378/165, 56, 54, 196, 146; 73/597, 592

(56) References Cited

U.S. PATENT DOCUMENTS 5,119,820 A * 6/1992 Rossman et al. ........... 600/449
5,840,029 A * 11/1998 Mazess et al. .............. 600/437
6,009,147 A * 12/1999 Stein et al. .................. 378/196

OTHER PUBLICATIONS

R.N. McCartney et al., "Combined 2.25 MHz ultrasound velocity and bone mineral density measurements in the equine metacarpus and their in vivo applications", Medical & Biological Engineering & Computing, Nov. 1987, pp. 620–626.

* cited by examiner

Primary Examiner—Marvin M. Lateef
Assistant Examiner—Ruby Jain
(74) Attorney, Agent, or Firm—McDermott, Will & Emery (57) ABSTRACT

A bone mineral density meter comprises first input device which enters a sound of speed in a bone; second input device which enters a weight of the person to be measured; third input device which enters fat free mass of the person to be measured; arithmetic device which computes the bone mineral density based on data from said first input device and data from said second input device and said third input device; and display which displays a bone mineral density value computed by said arithmetic device. The present invention allows a bone mineral density to be safely estimated, at a low cost, and with proper accuracy and without having to worry about exposure to X-rays.

19 Claims, 9 Drawing Sheets

| | | |
|---|---|---|
| HEIGHT | 888.8 | cm |
| AGE | 888.8 | AGE |
| WEIGHT | 888.8 | kg |
| PERCENT FAT | 888.8 | % |
| FFM | 888.8 | kg |
| BONE MINERAL DENSITY | 888.8 | g/cm² |
| DEGREE OF HEALTH BALANCE | EXCELLENT  GOOD  NORMAL  BAD | |

METHOD OF ESTIMATING BONE MINERAL DENSITY AND APPARATUS FOR ESTIMATING BONE MINERAL DENSITY

BACKGROUND OF THE INVENTION

1. Field of the Invention

The present invention relates to a method and an apparatus for estimating a Bone Mineral Density (hereinafter referred to as "BMD"), and in particular, to a method and an apparatus for estimating a Bone Mineral Density utilizing an ultrasound and a bioelectrical impedance.

2. Prior Art

With age, human bones tend to become more brittle, the ratio of fractures caused by falls etc. tends to increase, and it tends to take much more time to recover after such a fracture. For example, if an elderly person fractures a leg, the time period during which it is difficult to walk tends to become longer, and such a person may thus be requested to stay in bed. As a result, this person's everyday life is significantly effected, and further asthenia tends to progressively advance since it is impossible for this person to move and for other reasons.

Thus, as one of the means for judging the brittleness of human bones, a method and an apparatus for measuring BMD, which is one of the indexes of the degree of bone health, have been developed and are used at hospitals or the like. The term "BMD" herein refers to Bone Mineral Calcium (hereinafter referred to as "BMC") contained per unit area of the bone. Although a bone includes a bone radical component (fiber component) and a component of calcification, bone mass is referred to as the Bone Mineral Calcium, since, at the present time, when measuring the bone mass, calcification mass thereof is measured.

In consequence of the measurements made at hospitals etc. utilizing the above measuring method, we have learned that, among elderly people, there are a great many whose bones are in condition in which they easily fracture, that is, osteoporosis, and moreover, half of females more than 65 years old and half of males more than 80 years old are diagnosed as having osteoporosis, and thus this matter is becoming a very significant problem. Also, in recent years, not only among elderly people but also among youths, people who are diagnosed as having osteoporosis have been increasing due to the effects of a lack of exercise, an unbalanced diet, excessive dieting or the like. Also, invalids tend to get osteoporosis for reasons similar to the above given ones, and also expectant mothers are often said to easily get osteoporosis since a large amount of calcium in their bodies is consumed because of giving birth and breast feeding. Thus, it is possible to say that the risk of getting osteoporosis has become very high.

Consequently, various methods and apparatuses for determining the degree of bone health have been developed so as to prevent osteoporosis, and they can be categorized as follows:

(1) Simple X-ray Image

The determination of the degree of bone health will be made, based on an X-ray picture of a bone, by judging the degree of reduction of a calcium fiber, that is, calcification mass in a vertebra or a transcervical.

(2) Second Metacarpus Atrophy Degree Measurement Method (MD Method, DIP Method)

This is a method in which, by utilizing a computer, an X-ray picture of a bone is analyzed and then an atrophy degree of a bone is indicated by a numeral. In the MD method (Micro-Densitometry Method), a picture of a second metacarpus is taken using an X-ray and analyzed, while, in the DIP method (Digital Image Processing Method), an X-ray picture is transmitted to a high resolution processing equipment via a television camera for instrumentation, so that the bone mass can be estimated.

(3) Dual Energy X-ray Absorptiometry (DEXA Method)

This is a method in which, by utilizing two X-rays of different wavelengths, the bones of the umbar spine front, back and side, transcervical or the like are measured and analyzed. In this method, both a cortical bone and a cancellous bone are measured.

(4) QTC Method

This is a method in which an X-ray absorbed dose is estimated without a picture and the bone mass is estimated by a computer process. In this method, only a petrous cancellous bone of a spine can be measured in ring sections thereof without the effects of a bone deformation and a pool of calcium.

(5) Ultrasonography

This is a method in which an ultrasound signal is transmitted to a heel or the like and a stiffness of a bone is estimated based on a traveling speed of the ultrasound etc.

Figure 6:
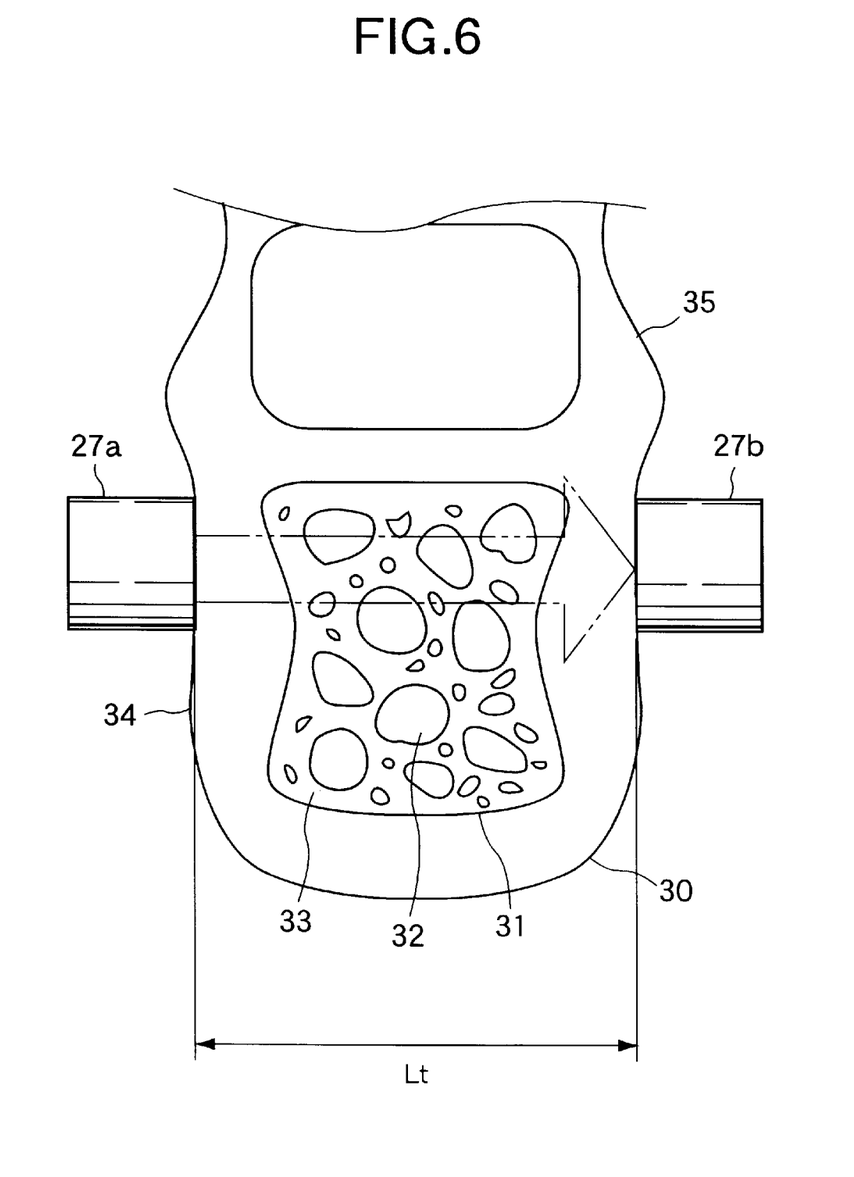
FIG. 6 is a diagram illustrating a principle of an ultrasonography.

Now, a principle of the ultrasonography will be described below. FIG. 6 is a diagram illustrating a principle of the ultrasonography. This figure shows a sectional view of a heel portion when the ultrasound has passed through a calcaneus. "30" indicates a heel, "31" indicates the calcaneus, "33" indicates a cortical bone which is a peripheral part of a bone and "32" indicates respective cancellous bones which are an inner part of a bone. "34" indicates a cutis and "35" indicates an ankle. "27a" indicates an ultrasound transmitter for transmitting the ultrasound and "27b" indicates an ultrasound receiver for receiving the ultrasound which has passed through the calcaneus.

Even if a bone is thin, if the cortical bone 33 thereof is thick and the cancellous bones 32 thereof are densified, such a bone is resistant to fracture. On the contrary, even if a bone is thick, if the cortical bone 33 thereof is thin and the cancellous bones 32 thereof each have a space therein (loose condition), such a bone is brittle and thus easy to fracture. Thus, it is necessary to comprehensively judge both the thickness of the cortical bone 33 and the condition of the cancellous bones.

A cell such as a cutis has almost the same acoustic character as that of water, and a sound can be transmitted therethrough at a speed of 1500 m/s, an attenuation thereof caused by such transmission being small. Compared to an ordinary cell, a bone is very hard, a speed of sound transmitted therethrough is fast and an attenuation thereof caused by such transmission becomes great. When osteoporosis occurs, the cortical bone 33 is decreased in width, a medullary cavity is increased, and in each of the cancellous bones 32, a trabeculae thereof is decreased and rarified. Since most parts of the rarified medullary cavity are filled with bone marrow liquid, the acoustic character of such a rarified bone becomes more similar to that of water in comparison with that of a healthy bone. That is, as compared to the healthy bone, the speed of sound transmitted through the rarified bone is slow and the attenuation thereof becomes small. Thus, an ultrasound is inputted into the bone from one side thereof and the time it takes for the ultrasound to reach the other side thereof is calculated, so that the calculated speed of sound should reflect the bone mineral density thereof.

As the calcaneus is relatively large and the side shape thereof is almost planar, it is easy to measure the length thereof and such a calcaneus can resist the effect of the sound wave diffracted from the cortical bone. Also, as it is clear that ninety percent of the content in the calcaneus are the cancellous bones, the calcaneus can be adequately measured by the ultrasound measuring method and is often measured by this method. Further, since the flesh portion covering the calcaneus is thin, if this measurement is made from the top of the cutis, any possible error in this measurement is not great.

Now, a method of obtaining a sound of speed SOS in the heel will be described. The time "T" that elapsed before the ultrasound, which is transmitted from the ultrasound transmitter $27a$, has passed through the calcaneus 31 and reached the ultrasound receiver $27b$, is measured. Assuming the distance between the transmitter and the receiver is "Lt", the equation:

$$SOS = Lt \div T \qquad \text{(equation 1)}$$

is satisfied.

Now, the method of obtaining the bone mineral density from the SOS will be described. For a number of subjects, their bone mineral densities BMDs are measured by utilizing the highly accurate DEXA method, and their SOSs are measured by means of the ultrasonography to obtain a regression equation between the BMDs and the SOSs. By utilizing such a correlation equation, the bone densities can be obtained from the SOSs.

In addition to the above, in the ultrasonographical methods, there is another type of method which indicates, by means of a frequency analysis, the conditions of the bones accurately by utilizing the fact that the attenuation rates obtained when the ultrasound has passed through the bones are different from one another.

However, since all of the methods described in the above items (1) to (4) utilize an X-ray, the assistance of a radiological technician is indispensable, which creates an obstacle to the widespread use thereof. Also, these methods are not preferable in that the people to be measured are exposed to an X-ray radiation and also that these methods become expensive. On the other hand, the method described in the above item (5) is preferable because the cost thereof is relatively small in comparison with that of the methods described in the above items (1) to (4), and does not utilize an X-ray.

However, a bone is considerably non-uniform in a structure of the trabeculae thereof. Further, although the bone mass of the portion of the bone near the cortical bone 33 is large, the bone mass decreases gradually toward the center of the bone. Thus, there is a problem that the measured values can vary depending on the portion of the bone through which the ultrasound has passed. Further, since the cancellous bone is a sparse bone including some portions having no bone and other portions having bone, the situations at the same portions of the bone and of the portions of the bone having the same bone mineral density can vary from person to person, and whether the trabeculae is present or not can change depending on the portions of the bone through which the ultrasounds have passed, and thus the resultant acoustic characters of bones such as SOSs can differ from bone to bone.

Also, although the portions of a bone where the measurements can be made are limited to specific portions such as the calcaneus etc., the portions where fractures actually easily occur are portions such as the umbar spine, thigh bone or the like. As the bone mineral densities vary from person to person at each of the portions, it is not possible to accurately determine the bone mineral density based on only the specific locations. Thus, the ultrasonography has a problem in that many errors occur when it is used.

The object of the present invention is, in view of the above described present circumstances, to provide a method of estimating bone mineral density which enables anyone to estimate their bone mineral density safely, at a low cost, and with proper accuracy, without worrying about exposure to X-rays.

SUMMARY OF THE INVENTION

According to an aspect of the present invention, there is provided a method of estimating a bone mineral density wherein the bone mineral density of a person to be measured is estimated based on an arithmetic expression using a sound of speed in a bone, a weight, and fat free mass of the person to be measured as parameters.

According to one embodiment of the present invention, said arithmetic expression is expressed by $BMD = C_1 \times SOS + C_2 \times Wt + C_3 \times FFM + C_4$, where the sound of speed in the bone is SOS, the weight is Wt, the fat free mass is FFM, the bone mineral density is BMD, and the constants are $C_1$, $C_2$, $C_3$, and $C_4$.

According to another embodiment of the present invention, in said arithmetic expression, a correction is made thereto based on personal parameters of height, sex, age, presence or absence of menstruation, age at menopause, and years which elapsed since the beginning of menopause in the person to be measured.

According to another aspect of the present invention, there is provided a method for estimating a bone mineral density wherein the bone mineral density of a person to be measured is estimated based on an arithmetic expression using at least one of a weight, fat free mass, or cell mass and a sound of speed in a bone of the person to be measured as parameters.

According to further aspect of the present invention, there is provided an apparatus for estimating a bone mineral density comprising: first input device which enters a sound of speed in a bone of a person to be measured; second input device which enters a weight of the person to be measured; third input device which enters fat free mass of the person to be measured; arithmetic device which computes the bone mineral density based on data from said first input device, said second input device and said third input device; and display which displays a bone mineral density value computed by said arithmetic device.

According to one embodiment of the present invention, said display displays a percentage of the bone mineral density computed by said arithmetic device in comparison with a Young Adult Mean of bone mineral densities and a result determined on the basis of the percentage.

According to another embodiment of the present invention, the determined result being that, if the percentage is within 70% to 80%, a decrease in the bone mass is suspected and that, if the percentage is less than 70%, osteoporosis is suspected.

According to one embodiment of the present invention, said display displays a graphical representation in which the bone mineral density is shown in X-axis and at least one of height, weight, age, percent fat and fat free mass is shown in Y-axis, and it further displays a graphical representation of the Young Adult Mean of bone mineral densities.

According to another embodiment of the present invention, said apparatus further comprising fourth input device which enters a percent fat of the person to be measured and health balance computing device which computes a health balance index on the basis of the bone mineral density value computed by said arithmetic device and the percent fat entered from said fourth input device.

According to one embodiment of the present invention, a value of the health balance index is at least any one of excellent, good, normal and bad values.

According to another embodiment of the present invention, said first input device is an ultrasound transducer.

According to one embodiment of the present invention, said first input device is key device for enabling said sound of speed to be manually entered.

According to another embodiment of the present invention, said second input device is a weight sensor.

According to one embodiment of the present invention, said second input device is key device for enabling the weight of the person to be measured to be manually entered.

According to another embodiment of the present invention, said third input device is a part for measuring the fat free mass.

According to one embodiment of the present invention, said second input device is key device for enabling the fat free mass to be manually entered.

According to another embodiment of the present invention, said second input device and said third input device are each a scale with a body fat measuring apparatus.

According to one embodiment of the present invention, said arithmetic device is computed based on an arithmetic expression expressed by $BMD=C_1 \times SOS+C_2 \times Wt+C_3 \times FFM+C_4$, where the sound of speed in the bone is SOS, the weight is Wt, the fat free mass is FFM, the bone mineral density is BMD, and the constants are $C_1$, $C_2$, $C_3$, and $C_4$.

According to another embodiment of the present invention, in said arithmetic expression, a correction is made thereto based on personal parameters of height, sex, age, presence or absence of menstruation, age at menopause, and years which elapsed since the beginning of menopause in the person to be measured.

DESCRIPTION OF PREFERRED EMBODIMENTS

Now, based on the accompanying drawings, the present invention will be described in more detail for the embodiments and examples of the present invention.

First, a method of estimating a bone mineral density which is underlying the present invention, will be explained. Initially, it should be noted that how a bone becomes healthy. Calcium is being melted out from a bone so as to keep a calcium density in blood at a constant level. The calcium can continuously be replenished to the bone by the ingestion of calcium and vitamin D and the outdoor exercise. Therefore, even if the ingestion of calcium and vitamin D was enough, if no exercise has been done, he may get osteoporosis. By providing a load (a weight) to the bone in a gravity direction, it is possible to say that the bone can be getting health. It is known that a weight and a bone mineral density have an advantageous correlation therebetween, and the above description supports this.

Figure 7:
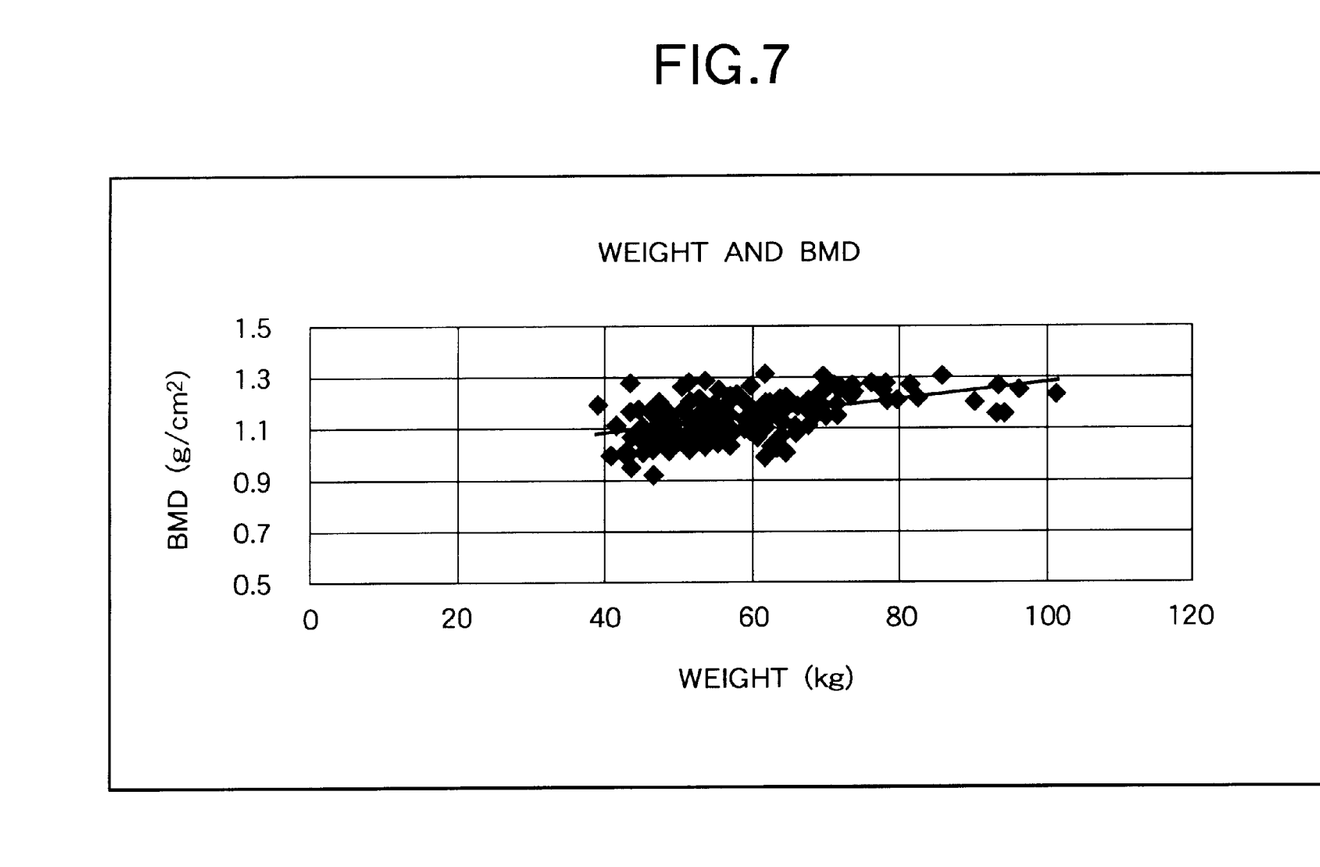
FIG. 7 is a diagram showing a graph of weights and results of bone mineral densities measured by utilizing a DEXA method.

FIG. 7 is a graphic representation for 160 able-bodied women, of their weights and their results of the bone mineral densities measured by utilizing a DEXA method. A correlation coefficient obtained by a regression analysis is 0.521 and thus this shows a good correlation therebetween.

It is evident that this method is a very good approach equivalent to a bone mineral density measurement using the ultrasonography, from the fact that such data in FIG. 7 shows a clear correlation between a weight and a bone mineral density, despite that this data is for subjects whose average age is about 35, only 5 people among the subjects are over 60 years old and all the subjects are able-bodied people who do not have any serious troubles in regard to their bone mineral densities.

It is known that the bone mineral density is closely related to fat free mass. The fat free mass is a part of the body other than fats portions of the body and it consists of tissues such as cells, extracellular fluid, bones, etc. The fat free mass can be determined by the bioimpedance method. A fat layer in a living body allows a little electricity to flow therethrough, while cell tissues such as muscle etc. allow electricity to flow therethrough. Further intercellular fluid surrounding blood, lymph corpuscle and cells are good electrical conductors and electricity also flows through even a bone marrow of the bone. In the bioimpedance method, by utilizing the above fact, a little high frequency electricity is fed through the body so as to determine an electrical resistance value and thus to determine the fat free mass.

Figure 8:
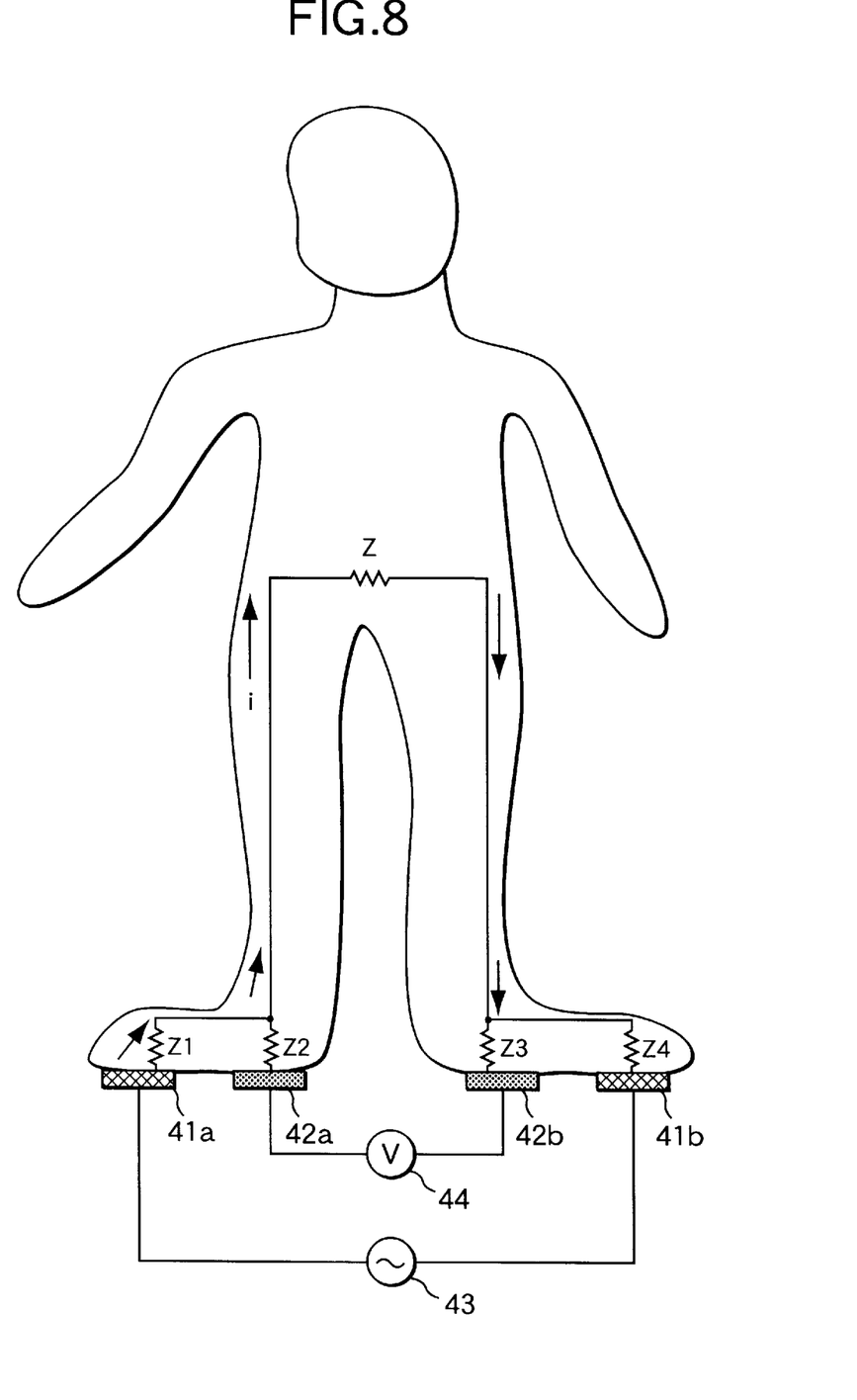
FIG. 8 is a diagram illustrating a method of measuring bioimpedance between feet.

Now, a method of determining the fat free mass from the electrical resistance value will be explained. FIG. 8 is a diagram illustrating a method of measuring bioimpedance between feet. Electrodes 41a and 41b for supplying electrical current are provided on the toes of the feet, respectively, and they are connected to an alternating current source 43. Also, alternating voltage electrodes 42a and 42b are respectively provided to the heels of the feet and they are connected to an alternating voltmeter 44. An alternating current "i" in the Figure flows through contact impedance Z1 of a cutis of one foot, a bioelectrical impedance between both feet, and contact impedance Z4 of a cutis of the other foot. A voltage difference V introduced by the bioimpedance is $$V = Z \times i.$$

The Voltage difference V can be measured accurately by utilizing the alternating voltmeter 44 having high input impedance, which is insensitive to the contact impedances Z2 and Z3 to the cutes of the heels.

Although, bioimpedances has generally been measured by measuring it between hands or between one hand and one foot, besides the above measuring of it between feet, in any measurement, a correlation between the resultant measurement and the whole-body composition is preferable, and it is possible to estimate the whole-body composition by measuring any portion of the body.

The following is a method for obtaining the fat free mass FFM based on the measurement value of the bioimpedance. Assuming the resistivity of a portion of the body other than fat portions of the body (a lean body) is $\rho$ per unit volume, the impedance Z is obtained by the equation $$Z = L \times \rho \div A$$

where "L" is a length of the portion and "A" is a cross section thereof.

Assuming a gravity of the lean body is "$\tau$", the FFM is determined by the equation $$FFM = L \times A \times \tau, \text{ and thus, the equation}$$

$$FFM = L^2 \times \rho \times \tau \div Z$$

is satisfied. Since a path length of a current, that is, a length of the feet, is almost proportional to a height, "L" can be replaced with that obtained by multiplying the height Ht by a proportional constant. Assuming "$\rho$" and "$\tau$" are constant values and defining the proportional constant K as $K = k^2 \times \rho \times \tau$, the FFM can be obtained by the equation $$FFM = Ht^2 \times K \div Z.$$

In addition, the fat mass FM can be obtained by the equation $$FM = W - FFM \quad \text{(equation 2)}$$

where "W" is a weight.

Also, a percent fat "% FAT" is obtained by the equation $$\%FAT = FM \div W.$$

Figure 9:
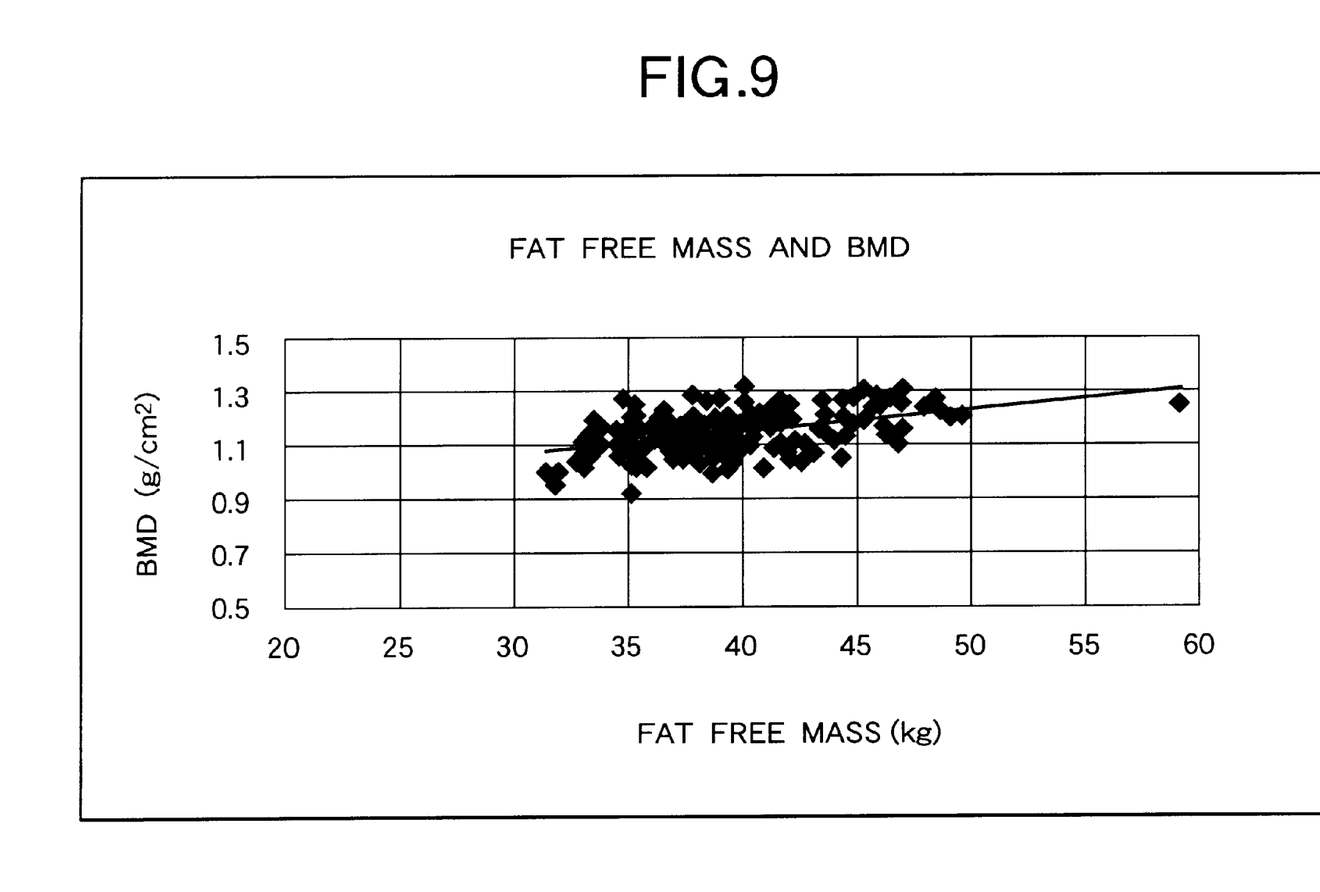
FIG. 9 is a diagram showing a graph of results of bone mineral density measured by utilizing a DEXA method and fat free mass measured by utilizing a bioimpedance method.

FIG. 9 is a graphical representation of results of measuring the bone mineral density by utilizing the DEXA method and the results of measuring the fat free mass by utilizing the bioimpedance method. The correlation coefficient is 0.627, it being understood that such a correlation is better than that between the bone mineral densities and the weights.

Further, the bone mineral density shows a good correlation with an amount of muscle. Since cell mass mainly depends on the muscle amount, if the cell mass can be estimated, it is possible to improve the accuracy of an estimation of the bone mineral density. Because of the development of the bioimpedance method in recent years, a new method has been suggested in which the cell mass can be directly calculated. Since a cell film is made of fat, it is an insulation, and thus the direct current does not pass therethrough. However, since such a cell film is very thin, it is equivalent to a capacitor, and thus an alternating current can pass therethrough, and the bioimpedance can be changed due to the frequency of such a current.

In the case of a current having an extremely low frequency, since most of the current does not pass through the cell film and it passes only through the extracellular fluid, the amount of such extracellular fluid can be calculated. On the other hand, in the case of a current having an extremely high frequency, since the cell film can be a preferable conductor and the current can pass through both the extracellular fluid and cell fluid, the total amount of the extracellular fluid and the cell fluid can be calculated. Thus, the amount of the cell fluid, that is, the cell mass can be calculated.

The inventor has measured the BMDs, SOSs, weights Wts, and FFMs and made regression analyses.

The correlation coefficient between the BMDs and SOSs is 0.49.

When a multiple regression analysis is applied thereto, in which the BMDs are used as object variables and the SOSs and the weights are used as explanatory variables, a coefficient of a multiple correlation is 0.57.

When a multiple regression analysis is applied thereto, in which the BMDs are used as object variables and the SOSs and the FFMs are used as explanatory variables, a coefficient of a multiple correlation is 0.66.

When a multiple regression analysis is applied thereto, in which the BMDs are used as object variables and the SOSs, the weights and the FFMs are used as explanatory variables, a coefficient of a multiple correlation is 0.71.

The following regression equation can be obtained by the above correlation:

$$BMD = C_1 \times SOS + C_2 \times Wt + C_3 \times FFM + C_4 \quad \text{(equation 4)}$$

where $C_1$ to $C_4$ are constants. Thus, the bone mineral density BMD can be obtained by substitutions of the SOS that is determined by the sound of speed in the heel, Wt, and the FFM which is determined by the bioelectrical impedance, into the equation (4).

It is known that the constants $C_1$ to $C_4$ can change depending on personal parameters such as height, sex, age, presence or absence of menstruation, age at menopause, and years which elapsed since the beginning of menopause. Thus, the bone mineral density can be estimated more accurately by correcting the constants based on these personal parameters.

An apparatus for estimating the bone mineral density will now be described by way of example of the present invention as described above.

Figure 1:
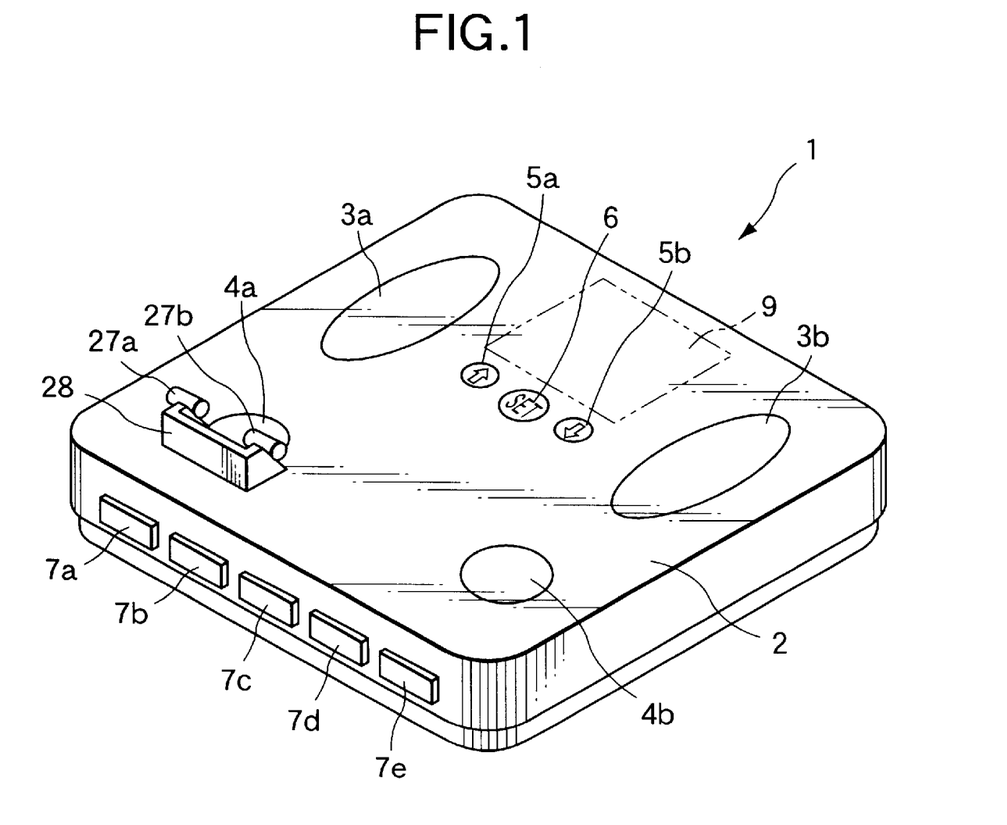
FIG. 1 is a schematic perspective view showing an appearance of an apparatus for estimating a bone mineral density in accordance with an embodiment of the present invention.
Figure 2:
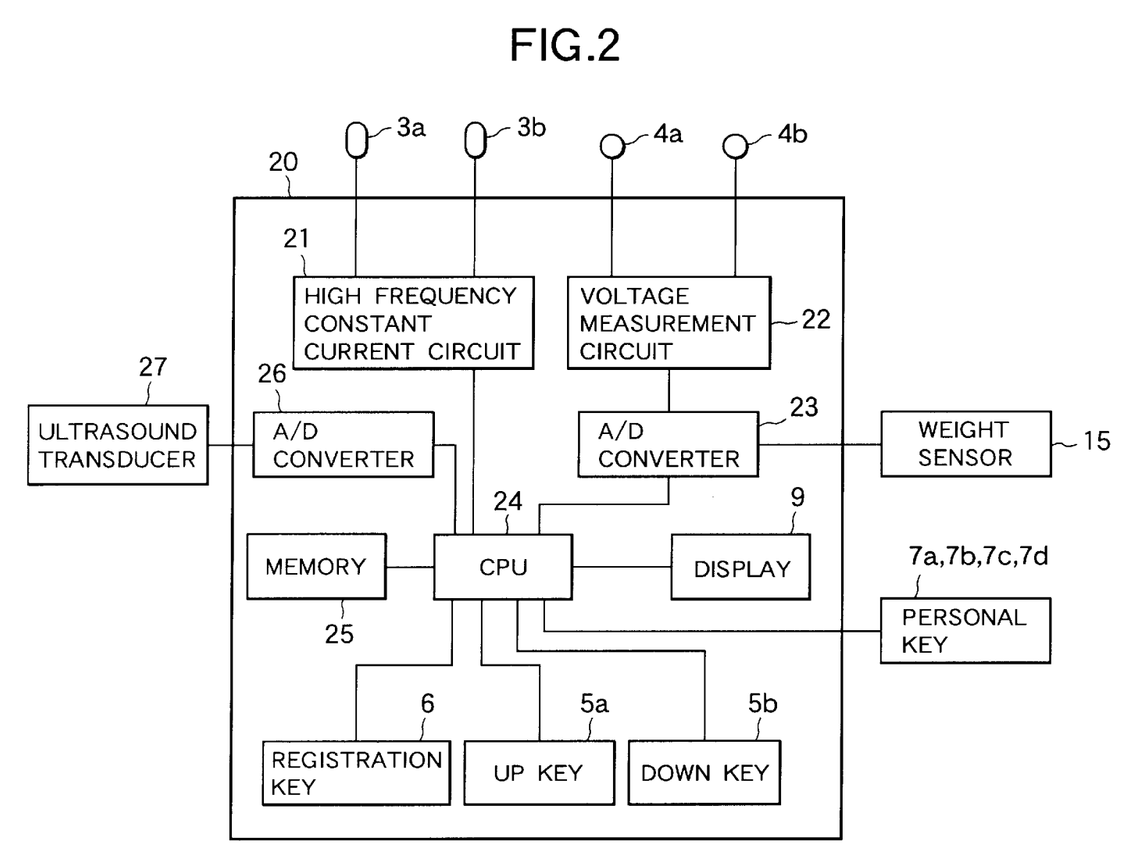
FIG. 2 is a block diagram showing an electrical circuit configuration of the apparatus in FIG. 1.

FIG. 1 is a schematic perspective view showing an appearance of an apparatus for estimating the bone mineral density and FIG. 2 is a block diagram showing an electrical circuit arrangement of the apparatus in FIG. 1. The estimating apparatus 1 in this embodiment comprises, on a weighing platform 2 of a scale, current-carrying electrodes 3a, 3b for forming a current path through a living body; measuring electrodes 4a, 4b for detecting a potential difference occurring in the living body; a registration key 6 for setting and registering personal conditions and for setting time; an UP key 5a for increasing values; a DOWN key 5b for decreasing values; personal keys 7a to 7e for making a measurement based on personal set and registered conditions; a display part 9 for displaying the situation of the set and registered conditions, measurement results or results of determinations; an ultrasound transmitter 27a; an ultrasound receiver 27b; and a heel guide 28 for positioning the heel at a correct position. Also, as shown in FIG. 2, inside the platform 2, a weight sensor 15 for detecting a load and transforming it to an electrical signal, an electronic circuit board 20, or the like. The personal keys 7a to 7e have or the registration key 6 has a function of a power switch, and upon depressing any one of the personal keys or the registration key, the power is turned on. Further, when a predetermined time has elapsed after the measurement results have been displayed, the power is turned off.

The electronic circuit board 20 is equipped with the display part 9 provided on the platform 2; the registration key 6; the UP key 5a; the DOWN key 5b; a high frequency constant current circuit 21 for applying a high frequency faint constant current to the current-carrying electrodes 3a, 3b; a voltage measuring circuit 22 for measuring the potential difference in the living body developed across the measuring electrodes 4a, 4b; an A/D converter circuit 23 for converting an analog signal from the voltage measuring circuit 22 or the weight sensor 15 to a digital signal; an A/D converter circuit 26 for converting an analog signal from the ultrasound transducer 27 to a digital signal; a memory 25 for storing the set and registered conditions, the measured data etc.; a CPU 24 for processing computation, control, or the like of a percent fat based on measurement conditions, and the measured bioimpedance data and weight data. The electronic circuit board 20 and the current-carrying electrodes 3a, 3b, the measuring electrodes 4a, 4b, the weight sensor 15, the ultrasound receiver 27, and the personal keys 7a, 7b, 7c and 7d are connected therebetween via an electric wire.

Figure 3:
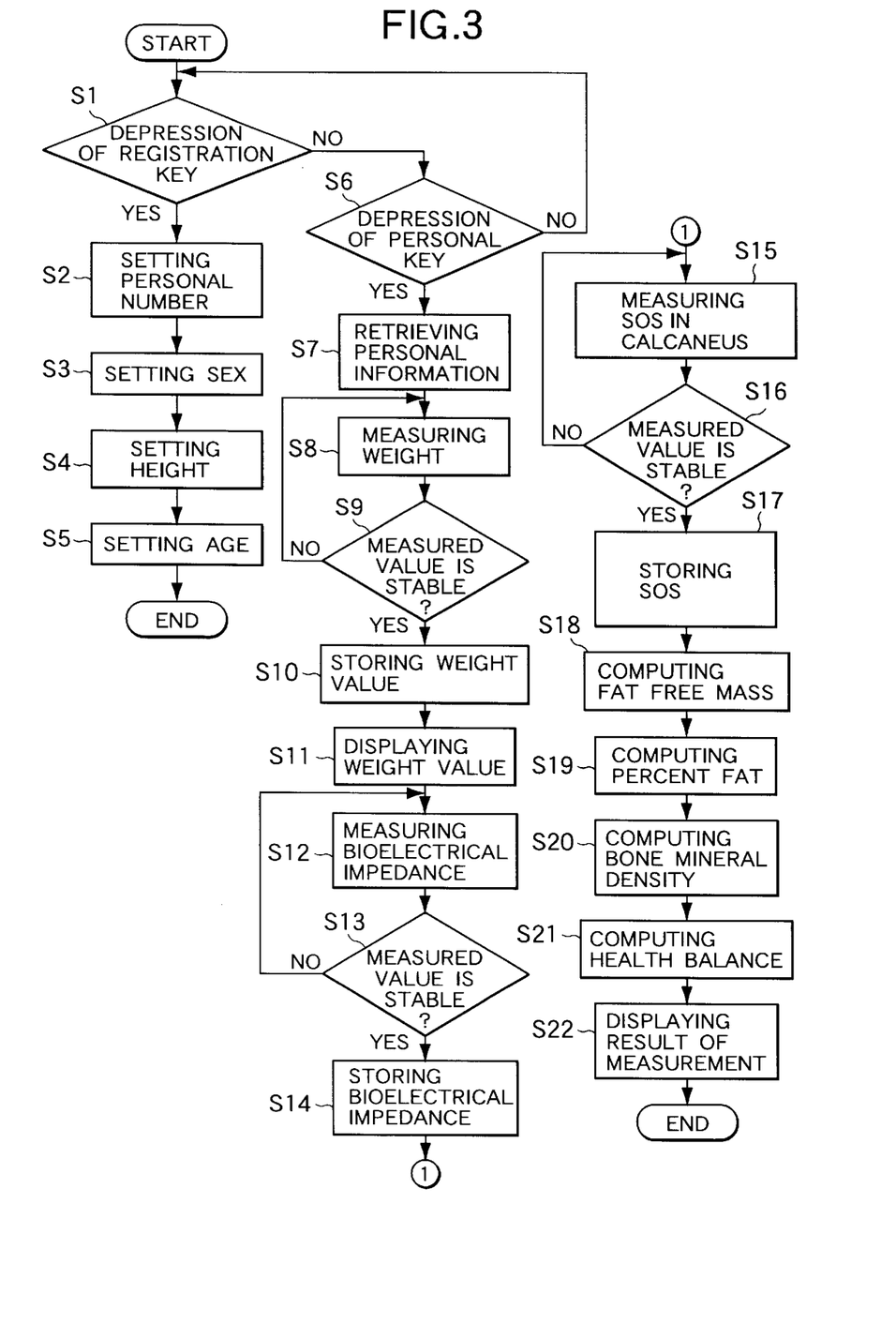
FIG. 3 is a flow chart illustrating a measurement and estimation procedure and an operational summary for estimating a bone mineral density, which is used in the apparatus in FIG. 1.

FIG. 3 is a flow chart illustrating a procedure for measuring and estimating the bone mineral densities and a summary of the operations performed by the apparatus for estimating a bone mineral density in accordance with the present embodiment. The overall operations will now be described below, with reference to the flow chart. Steps S2 to S5 will be simply described since these are prior art. In step S1, the determination is made whether the registration key 6 has been depressed. If the key which has been depressed is not the registration key 6, then the process goes to step S6. In step S2, a personal number is entered to set. On the display part 9, the personal number "1" is displayed. Upon depressing the UP key 5a, the personal number is increased one number at a time. Upon depressing the DOWN key 5b, the personal number is decreased one number at a time. Upon depressing the registration key 6, the personal number is set and the set number is then stored in the memory 25. In step S3, the sex of the person is entered to set it in a manner similar to that for setting the personal number. In step S4, the height of the person is set. In this step, since the initial value of the height is displayed on the display part 9, the value can be increased or decreased by utilizing the UP key 5a and the DOWN key 5b. When the value becomes a desired value, the height value is fixed by depressing the registration key 6. In step S5, the age of the person is set in a manner similar to that for setting the height, and then the program is terminated.

In step S6, if the key which is depressed is not any of the personal keys 7a to 7d, then the process returns to the step S1. In step S7, the information on the person's sex, height or the like which corresponds to the respective personal keys is retrieved from the memory 25 and displayed on the display part 9, and the operator is encouraged to check whether the personal key has been erroneously depressed. In step S8, when the person to be measured is loaded on the platform 2, his weight is measured. In step S9, if the measured value does not remain stable, then the process returns to the step S8. In step S10, the weight value is stored in the memory 25. In step 11, the weight value is displayed on the display part 9.

In step S12, the bioelectrical impedance will be measured as described below. That is, the high frequency constant current circuit 21 outputs a high frequency faint constant current I. This output current is applied to the person to be measured via the current-carrying electrodes 3a, 3b. At this time, the current passing through the person to be measured is detected by the voltage measuring circuit 22 as a potential difference in the living body developed across the measuring electrodes 4a, 4b. This analog output is converted to a digital signal V by the A/D converter 23. The bioimpedance Z is determined by the equation $Z=V/I$. In step S13, if the measured value does not remain stable, then the process returns to the step S12. In step S14, the measured bioelecrical impedance value is stored in the memory 25.

In step 15, the Sound of Speed SOS in the calcaneus is measured. The time "T" it takes for the ultrasound which has been transmitted from the ultrasound transmitter 27a, to pass through the calcaneus 31 and then reach the ultrasound receiver 27b is measured, and the SOS therefor is determined by using the equation 1. In step S16, if the measured value does not remain stable, then the process returns to the step S15. In step S17, the obtained SOS is stored in the memory 25.

Then, the process goes to step 18 and, by using the above mentioned method, the fat free mass FFM is calculated from the bioelectrical impedance measurement value measured in step 12. In step S19, the percent fat is calculated based on the weight value, the FFM and the like which have been obtained before.

In step S20, the bone mineral density BMD is determined by using the equation 4.

In step S21, a health balance is calculated by the percent fat, the bone mineral density, the sex, the age and the height of the person.

Figure 4:
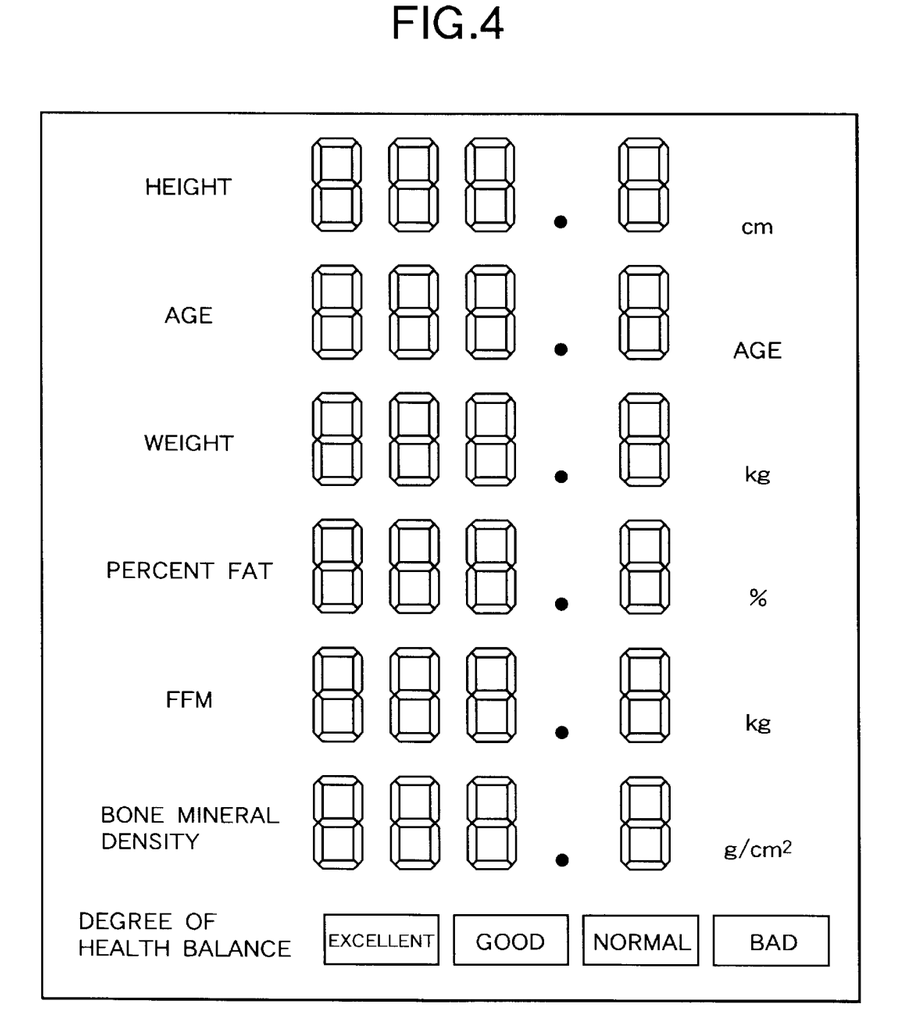
FIG. 4 is a diagram showing an example of a display of the apparatus in FIG. 1.

Then, the process goes to step S22, and as shown in FIG. 4, the measured values and the results calculated based on the measured values are displayed on the display part 9. Also, if standard values among coetaneous people, co-generation, etc. have been pre-stored in the memory 25, it is possible to display a determination index etc. for indicating how the measured values deviate from the standard values and so on. For example, if a Young Adult (20 to 44 years old) Mean "YAM" has been stored, then it is possible to display that, if the measured value is within 70% to 80% of the Mean, "a decrease in the bone mass is suspected", and if it is less than 70% thereof, "osteoporosis is suspected" or the like.

Figure 5:
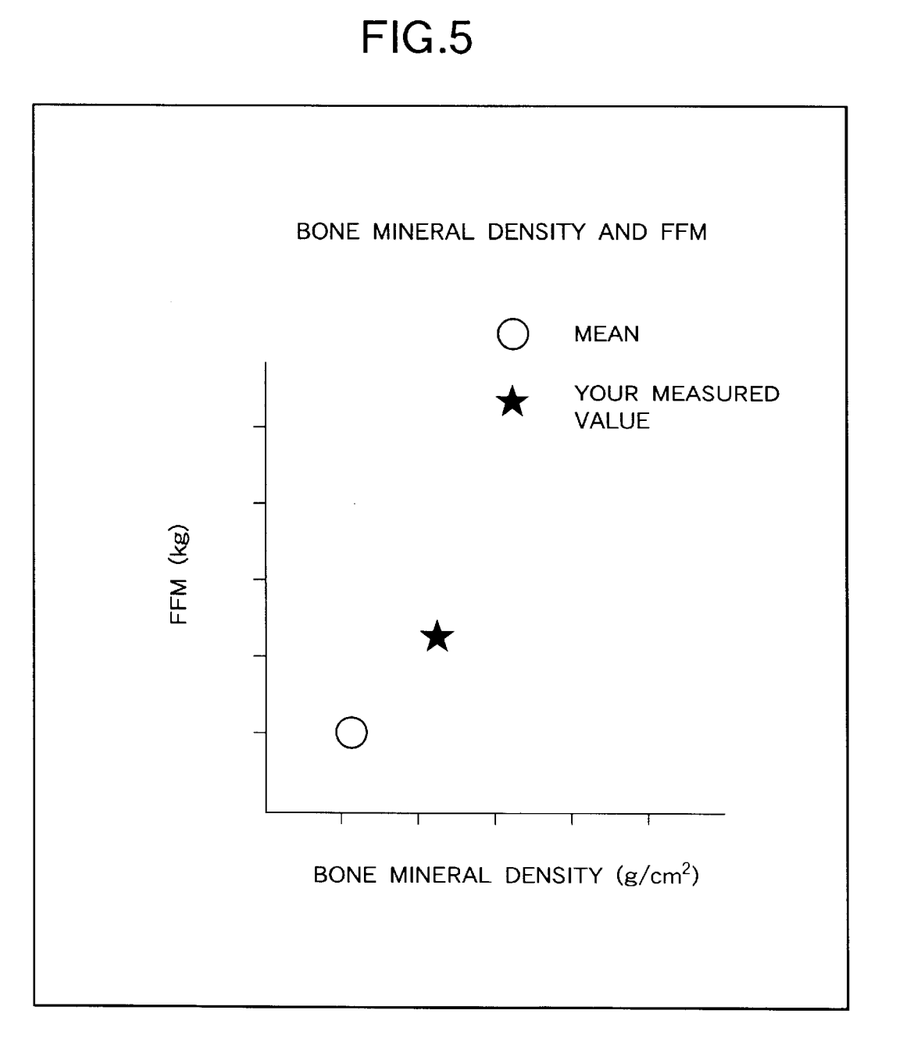
FIG. 5 is a diagram showing an example of a display of the apparatus in FIG. 1.

In addition, the above Mean and the measured personal data can be visually checked by plotting the bone mineral density, the SOS, etc. in the X-axis and the height, the weight, the age, the percent fat, the FFM, etc. in the Y-axis. FIG. 5 illustrates an example in which the bone mineral density is plotted in the X-axis and the FFM in the Y-axis.

The apparatus for estimating the bone mineral density of the present invention can also display the percent fat. It is possible for the person having a low bone mineral density to tend to get an adult disease, because if he eats too many nutritious foods to ingest calcium or the like so that his bone mineral density is increased but he forgets about the importance of exercise and thus does not exercise, he will get fat, even though his bone mineral density is increased to some extent because of an increase in his weight. On the contrary, if a fat person tries to get thinner by dieting, he tends to become dystrophic or to not do enough exercise and thus his bone mineral density decreases. By simultaneously displaying the percent fat and the bone mineral density, it is possible to encourage such a person to be measured to improve his condition without his having to proceed in the erroneous manner as described above, but to encourage him to improve his physical constitution while keeping his health balance. Also, by displaying the bone mineral density, the percent fat, and the weight, a health balance as to whether the bone mineral density, the percent fat, and the weight are proper or off-balance can be determined. Thus, it is possible to show a more proper health index.

The fat free mass FFM can be obtained by the following equation based on the equation 2 of the definition equation of the fat mass FM and the equation 3 of the definition equation of the percent fat, % FAT;

$$FFM = W \times (1 - \%FAT).$$

This equation means that if the weight and the percent fat are known, the fat free mass can be obtained. Thus, if the ultrasound transmitter and the prior art scale with a body fat measuring apparatuses are provided, all the input variables for obtaining the bone mineral density BMD in the equation 4 can be determined.

Since, in the present invention, the bone mineral density of the person to be measured is estimated based on an arithmetic expression using the sound of speed in the bone, the weight, and the fat free mass of the person to be measured as parameters, it is possible to estimate the bone mineral density without worrying about exposure to X-rays.

In addition, since said arithmetic expression of the present invention is expressed by $BMD = C_1 \times SOS + C_2 \times Wt + C_3 \times FFM + C_4$, where the sound of speed in the bone is SOS, the weight is Wt, the fat free mass is FFM, the bone mineral density is BMD, and the constants are $C_1$, $C_2$, $C_3$, and $C_4$, it is possible to accurately estimate the bone mineral density.

Further, since, in said arithmetic expression of the present invention, a correction is made thereto based on personal parameters of height, sex, age, presence or absence of menstruation, age at menopause, and years which elapsed since the beginning of menopause in the person to be measured, it is possible to further increase the accuracy of the estimation of the bone mineral density.

Further, since, in the present invention, the bone mineral density of the person to be measured is estimated based on the arithmetic expression using at least one of the weight, the fat free mass, or the cell mass and the sound of speed in the bone of the person to be measured as parameters, it is possible to improve the estimation accuracy.

Further, since, the present invention comprises first input device which enters the sound of speed in a bone of a person to be measured; second input device which enters a weight of the person to be measured; third input device which enters fat free mass of the person to be measured; arithmetic device which computes the bone mineral density based on data from said first input device, said second input device and said third input device; and which displays a bone mineral density value computed by said arithmetic device, it is possible to increase the accuracy of the estimation of the bone mineral density.

Further, since said second input device and said third input device of the present invention are each a scale with a body fat measuring apparatus, it is possible to effectively utilize the prior art.

Further, since said arithmetic device of the present invention is computed based on the arithmetic expression expressed by $BMD = C_1 \times SOS + C_2 \times Wt + C_3 \times FFM + C_4$, where the sound of speed in the bone is SOS, the weight is Wt, the fat free mass is FFM, the bone mineral density is BMD, and the constants are $C_1$, $C_2$, $C_3$, and $C_4$, it is possible to increase the accuracy of the estimation of the bone mineral density.

Further, since, in said arithmetic expression, a correction is made thereto based on personal parameters of height, sex, age, presence or absence of menstruation, age at menopause, and years which elapsed since the beginning of menopause in the person to be measured, it is possible to improve the accuracy of the estimation of the bone mineral density more.

As described above, in accordance with the present invention, since an X-ray is not used, there is no problem associated with exposure to X-rays and thus the present invention is safe. Also, since the assistance of a radiological technician is not indispensable for carrying out the present invention, the present invention can easily be carried out. Also, the bone mineral density can be estimated with proper accuracy.

Also, it is possible to provide an indicator of a person's eating tendencies or habits; to allow this person to gain a deeper understanding of nutrition and exercise; to provide suggestions about a method for improving a person's health while keeping his health balance; and to prevent a person from getting osteoporosis and having fractured bones.

What is claimed is:

1. A method of estimating a bone mineral density wherein the bone mineral density of a person to be measured is estimated based on an arithmetic expression using a sound of speed in a bone, a weight, and fat free mass of the person to be measured as parameters.

2. The method accordance to claim 1, said arithmetic expression is expressed by $$BMD = C_1 \times SOS + C_2 \times Wt + C_3 \times FFM + C_4$$

where SOS is the sound of speed in the bone, Wt is the weight, FFM is the fat free mass, BMD is the bone mineral density, and $C_1$, $C_2$, $C_3$, and $C_4$ are the constants.

3. The method according to claim 1 or 2, wherein, in said arithmetic expression, a correction is made thereto based on personal parameters of height, sex, age, presence or absence of menstruation, age at menopause, and years which elapsed since the beginning of menopause in the person to be measured.

4. A method for estimating a bone mineral density wherein the bone mineral density of a person to be measured is estimated based on an arithmetic expression using at least one of a weight, fat free mass, or cell mass and a sound of speed in a bone of the person to be measured as parameters.

5. An apparatus for estimating a bone mineral density comprising:

first input device which enters a sound of speed in a bone of a person to be measured;

second input device which enters a weight of the person to be measured;

third input device which enters fat free mass of the person to be measured;

arithmetic device which computes the bone mineral density based on data from said first input device, said second input device and said third input device; and display which displays a bone mineral density value computed by said arithmetic device.

6. The apparatus according to claim 5, wherein said display displays a percentage of the bone mineral density computed by said arithmetic device in comparison with a Young Adult Mean of bone mineral densities and a result determined on the basis of the percentage.

7. The apparatus according to claim 6, the determined result being that, if the percentage is within 70% to 80%, a decrease in the bone mass is suspected and that, if the percentage is less than 70%, osteoporosis is suspected.

8. The apparatus according to claim 5, wherein said display displays a graphical representation in which the bone mineral density is shown in X-axis and at least one of height, weight, age, percent fat and fat free mass is shown in Y-axis, and it further displays a graphical representation of the Young Adult Mean of bone mineral densities.

9. The apparatus according to claim 5, said apparatus further comprising fourth input device which enters a percent fat of the person to be measured and health balance computing device which computes a health balance index on the basis of the bone mineral density value computed by said arithmetic device and the percent fat entered from said fourth input device.

10. The apparatus according to claim 9, wherein a value of the health balance index is at least any one of excellent, good, normal and bad values.

11. The apparatus according to any one of claims 5 to 10, wherein said first input device is an ultrasound transducer.

12. The apparatus according to any one of claims 5 to 10, wherein said first input device is key device for enabling said sound of speed to be manually entered.

13. The apparatus according to any one of claims 5 to 12, wherein said second input device is a weight sensor.

14. The apparatus according to any one of claims 5 to 12, wherein said second input device is key device for enabling the weight of the person to be measured to be manually entered.

15. The apparatus according to any one of claims 5 to 14, wherein said third input device is a part for measuring the fat free mass.

16. The apparatus according to any one of claims 5 to 14, wherein said second input device is key device for enabling the fat free mass to be manually entered.

17. The apparatus according to any one of claims 5 to 12, wherein said second input device and said third input device are each a scale with a body fat measuring apparatus.

18. The apparatus according to any one of claims 5 to 17, wherein said arithmetic device is computed based on an arithmetic expression expressed by $$BMD = C_1 \times SOS + C_2 \times Wt + C_3 \times FFM + C_4$$

where SOS is the sound of speed in the bone, Wt is the weight, FFM is the fat free mass, BMD is the bone mineral density, and $C_1$, $C_2$, $C_3$, and $C_4$ are the constants.

19. The apparatus according to any one of claims 5 to 18, wherein, in said arithmetic expression, a correction is made thereto based on personal parameters of height, sex, age, presence or absence of menstruation, age at menopause, and years which elapsed since the beginning of menopause in the person to be measured.

\* \* \* \* \*